United States Patent
Zheng et al.

(10) Patent No.: US 9,889,023 B2
(45) Date of Patent: Feb. 13, 2018

(54) METHODS AND DEVICES FOR PATIENT-SPECIFIC ACETABULAR COMPONENT ALIGNMENT IN TOTAL HIP ARTHROPLASTY

(75) Inventors: Guoyan Zheng, Bern (CH); Xiao Dong, Duebendorf (CH); Lutz-Peter Nolte, Huenibach (CH)

(73) Assignee: UNIVERSITY OF BERN, Bern (CH)

( * ) Notice: Subject to any disclaimer, the term of this patent is extended or adjusted under 35 U.S.C. 154(b) by 386 days.

(21) Appl. No.: 13/378,616

(22) PCT Filed: Jun. 8, 2010

(86) PCT No.: PCT/EP2010/003418
§ 371 (c)(1),
(2), (4) Date: Mar. 25, 2012

(87) PCT Pub. No.: WO2010/145769
PCT Pub. Date: Dec. 23, 2010

(65) Prior Publication Data
US 2012/0172884 A1    Jul. 5, 2012

(30) Foreign Application Priority Data
Jun. 17, 2009    (EP) ................................ 09405102

(51) Int. Cl.
*A61F 2/46*    (2006.01)
(52) U.S. Cl.
CPC .......... *A61F 2/4657* (2013.01); *A61F 2/4609* (2013.01); *A61F 2002/4668* (2013.01)
(58) Field of Classification Search
CPC .................. A61F 2/4657; A61F 2/4609; A61F 2002/4668; A61B 19/201
See application file for complete search history.

(56) References Cited

U.S. PATENT DOCUMENTS 5,122,145 A * 6/1992 Fishbane ............ A61B 17/6425
606/102
5,700,268 A * 12/1997 Bertin .................... A61F 2/4657
606/102
(Continued)

FOREIGN PATENT DOCUMENTS

EP    1 561 438 A2    8/2005
GB    2 224 937    5/1990
WO    WO/2010/128320    * 11/2010    ............... A61F 2/46

*Primary Examiner* — Samuel Hanna
(74) *Attorney, Agent, or Firm* — Agris & Von Natzmer, LLP; Joyce Von Natzmer

(57) ABSTRACT

An acetabular component alignment device for total hip arthroplasty comprises a calibration component allowing for aligning a main instrument axis (5) of the acetabular component depending on a set of two patient specific calibration parameters relating to rotational offsets of the acetabular component, whereas the device is constructed in such a way that calibration parameters may be chosen such that a second parameter of the set of calibration parameters is adjustable independently from a first parameter of the set of calibration parameters by rotating the acetabular component around the main instrument axis (5) of the acetabular component. A method for obtaining patient specific calibration parameters for alignment of an acetabular component in total hip arthroplasty, comprises the steps of determining patient specific morphology information relating to a geometry of the patient's pelvis; and processing the patient specific morphology information for obtaining a set of two patient specific calibration parameters relating to rotational offsets of the acetabular component. The calibration parameters are chosen such that a second parameter of the set of calibration parameters may be adjusted independently from a first parameter of the set of calibration parameters by rotating the acetabular component around a main instrument axis of the acetabular component.

7 Claims, 5 Drawing Sheets

(56) References Cited

U.S. PATENT DOCUMENTS

| | | | |
|---|---|---|---|
| 5,951,564 A * | 9/1999 | Schroder et al. ............. | 606/100 |
| 6,395,005 B1 | 5/2002 | Lovell | |
| 2004/0073225 A1* | 4/2004 | Subba Rao .................... | 606/91 |
| 2004/0220567 A1* | 11/2004 | Eisermann ......... | A61B 17/1642 |
| | | | 606/86 A |
| 2006/0184177 A1* | 8/2006 | Echeverri .......... | A61B 17/1746 |
| | | | 606/91 |

* cited by examiner

METHODS AND DEVICES FOR PATIENT-SPECIFIC ACETABULAR COMPONENT ALIGNMENT IN TOTAL HIP ARTHROPLASTY

CROSS-REFERENCE TO RELATED APPLICATIONS

This is the U.S. national stage of International application PCT/EP2010/003418, filed Jun. 8, 2010 designating the United States claiming priority to European application EP 09405102.6, filed Jun. 17, 2009.

TECHNICAL FIELD

The invention relates to an acetabular component alignment device for total hip arthroplasty and a method for obtaining patient specific morphology information for alignment of an acetabular component in total hip arthroplasty. The invention further relates to a method for obtaining patient specific calibration parameters for alignment of an acetabular component in total hip arthroplasty.

BACKGROUND ART

Optimal component placement continues to be a surgical challenge in total hip Arthroplasty (THA), especially for the less-experienced surgeon. Dislocation and subluxation are still the most frequent early complications. Failure to achieve joint stability necessitates revision surgery in many cases, significantly increasing morbidity for the patient and cost to the healthcare system.

Dislocation and subluxation have been well correlated to implant impingement caused by malpositioning of components. Angular orientation in terms of anteversion/antetorsion and inclination has been identified as the related geometric key factor. Excessive anteversion or inclination is one of the most common surgical errors resulting in dislocation. It is known that there is a statistically significant relationship between the increased acetabular component anteversion and the increased anterior dislocations. Furthermore, the risk of dislocation is significantly higher in those who have already experienced dislocation or after revision surgery. As the patients undergoing revision surgery will have more health problems, obtaining proper cup positioning during the primary surgery is crucial.

The optimal ranges of anteversion and inclination of the acetabular component have been extensively debated in the literature. Several so-called "safe zone" have been suggested. Lewinnek et al. (Lewinnek G E, Lewis J L et al: Dislocation after total hip-replacement arthroplasties. J Bone Joing Surg 60A:217, 1978) describes a safe zone of 5° to 25° for anteversion and 30° to 50° for inclination. They found that acetabular cups placed outside this safe zone were approximately four times as likely to dislocate. In a prospective study of 441 THAs, McCollum and Gray determined that the safe range for cup position was 30°-50° abduction and 20°-40° flexion (McCollum D E, Gray W J G: Dislocation after Total Hip Arthroplasty. Causes and Prevention. Clin Orthop 261:159-70, 1990).

Optimal cup positioning requires that the surgeon attains adequate anteversion and inclination of the acetabular component with respect to each individual pelvis morphology in a reproducible basis. The intra-operative mechanical guides, though easy to use, does not respect the individual pelvis morphology and utilize the plane of the operating room table as a reference when orienting the cup. This results in hips that are implanted outside the safe zone defined by Lewinnek et al. using only the mechanical guidance.

Recently, several groups (Asayama I., et al.: Intraoperative pelvic motion in total hip Arthroplasty. J. Arthroplasty, 19(8): 992-997, 2004; Ezoe M., et al.: Pelvic motion during total hip Arthroplasty with translateral and posterolateral approaches. J Orthop Sci 10: 167-172, 2005; Wilairatana V. and Prasongchin P.: Acetabular position setting in total hip Arthroplasty by using V-Inclinometer. J Med Assoc Thai, 87(4): 353-355, 2004; Echeverri S., et al.: Reliable acetabular cup orientation with a new gravity-assisted guidance system. J. Arthroplasty 21(3): 413-419, 2006; Echeverri S.: Orientation device for surgical implement. International Patent Application Number: PCT/CH2004/000466) described methods to use the constant direction of the force of gravity as a reference in THA. Asayama et al. introduced a 3-direction indicator to control intra-operative pelvic motion during THAs. The 3-direction indicator incorporates a digital compass with 2 goniometers, as well as a pendulum and target apparatus. It allows for controlling pelvic motion by measuring the three-dimensional (3D) angle formed by the gravitational direction and the Steinmann pin inserted into the iliac bone to fix the direction indicator. Using a pendulum and a goniometer, Wilairatana and Prasonchin proposed a so-called V-Inclinometer to measure the pelvic inclination. Different from these systems, Echeverri et al. described a gravity-assisted navigation system (GANS) to control both the pelvic motion and the acetabular component placement. Their system requires two bull's-eye bubble levels with one designed for controlling the pelvic motion in strict lateral decubitus and the other for controlling cup orientation for targeted anteversion and inclination. Like any other mechanical guide, this system is simple to use, but it is also highly flawed. This is due to the fact that the alignment system developed by Echeverri et al. was calibrated only with respect to one pelvis without considering the morphological difference between the future pelvis to be navigated and the pelvis used for calibration. It simply does not work due to the inherent morphological variations in human being. A recent simulation study of this method on 48 patient data revealed a maximum anteversion error of as high as 15° (Dong X, Echeverri S, Nolte L-P, Vallotton J, and Zheng G: Acetabular cup orientation using a statistical data based calibration table. In proceedings of the 8th Annual Meeting of the International Society for Computer Assisted Orthopaedic Surgery, Hongkong, China, Jun. 4-7, 2008. PP. 262-265).

In principle, computer-assisted THA Systems such as CT-based computer aided THA, fluoroscopy-based computer aided THA or image-free navigation allow for better component placement. However, due to the costs of the equipment as well as its service and maintenance, these techniques are very expensive. Furthermore, these systems are very complex and require additional training for the users.

SUMMARY OF THE INVENTION

It is the object of the invention to create methods and devices pertaining to the technical field initially mentioned, that allow for THA procedures that are comparably inexpensive and allow for high precision and optimal cup positioning at the same time.

The solution of the invention is specified by the features of claim 1. An acetabular component alignment device for total hip arthroplasty according to the invention comprises a calibration component allowing for aligning a main instrument axis of the acetabular component depending on a set of two patient specific calibration parameters relating to rotational offsets of the acetabular component. The calibration parameters are chosen such that a second parameter of the set of calibration parameters may be adjusted independently from a first parameter of the set of calibration parameters by rotating the acetabular component around the main instrument axis of the acetabular component.

This device constitutes a simple system where the gravity force direction may be used as a reference. It is very easy to handle and makes sure that the attention focus of the user (i. e. the surgeon) rests on the operation site.

The patient-specific acetabular component alignment device may be an adaptation of a conventional cup placement instrument such as a reamer or an impactor to incorporate a patient-specific feature or it may be attached to such a conventional instrument.

Preferably, the alignment device comprises an alignment component allowing for pointing to a position of the anterior superior iliac spine (ASIS) of an operating side of the patient's pelvis.

In a first preferred embodiment, the alignment component is a curved rod, whereas the rod and the main instrument axis defining an Instrument-Design Plane (IDP). In a second preferred embodiment, the alignment component is a laser line projector.

Advantageously, the calibration component comprises a calibration block having a plurality of attachment sites allowing for attaching a two-dimensional inclination indicator. A first attachment site corresponds to a first inclination relative to the instrument main axis and a second attachment site corresponds to a second inclination relative to the instrument main axis, whereas the first inclination is different from the second inclination. The different inclinations correspond to different values of at least one of the patient specific calibration parameters. Preferably, the different inclinations correspond to different values of a first of the calibration parameters, independent of the value of the second calibration parameter.

Usually, the values of the parameters representing the acquired patient specific morphology information will be continuous. However, as the relation between the calibration parameters and the parameter values will be continuous and as the required precision is usually only a few degrees, it is possible to provide calibration for a limited number of calibration angles, i. e. to provide a finite number of attachment sites.

In a preferred embodiment, the inclination indicator is a bull's eye (i. e. 2-dimensional) bubble level indicator being attachable to the calibration block. Preferably, the bubble level indicator comprises an attachment pin and whereas the attachment sites of the calibration block are constituted by differently oriented receptacle holes adapted to accommodate the pin of the bubble level indicator to be attached.

The navigational part (bubble level) is close to the surgical site and in the surgeon's visual focus.

Alternatively, the inclination indicator is an electronic inclination indicator, in particular a digital compass or an accelerometer. Such an indicator may be used together with the calibration block, or the calibration is effected electronically within the electronic indicator, e. g. by feeding in the calibration parameters.

Preferably, the calibration block is rotatable relative to the instrument main axis in order to calibrate the component depending on the patient specific calibration parameters.

Preferentially, the alignment device comprises a scale 12 relating a rotational position of the calibration block about the instrument main axis to a value of one of the patient specific calibration parameters. Most preferably, the rotational position of the calibration block relates to the second calibration parameter, independent of the first calibration parameter (whereas the first parameter defines the attachment site to be used).

In the context of a method according to the invention for obtaining patient specific calibration parameters for alignment of an acetabular component in total hip arthroplasty, the following steps are carried out:

a) determining patient specific morphology information relating to a geometry of the patient's pelvis;
b) processing the patient specific morphology information for obtaining a set of two patient specific calibration parameters relating to rotational offsets of the acetabular component;

whereas the calibration parameters are chosen such that a second parameter of the set of calibration parameters may be adjusted independently from a first parameter of the set of calibration parameters by rotating the acetabular component around a main instrument axis of the acetabular component.

The choice of parameters allows for the combining the accuracy achieved by a computer-assisted, patient-specific calibration with an easy-to-handle mechanical guide such as the inventive acetabular component alignment device as described above. The accuracy that may be reached is comparable to a (much more expensive and complicated) image-free navigation system. It is to be noted that the specific choice of parameters targets for the lateral approach, which is the standard approach that is used most widely.

Preferably, the patient specific morphology information comprises:

c) an angle between the Anterior Pelvic Plane (APP) of the pelvis and an Intra-Operative Reference Plane (IRP) of the patient's pelvis; and
d) an orientation of the vector from an acetabular center to the anterior superior iliac spine (ASIS) of an operating side of the patient's pelvis with respect to a local coordinate system of the Intra-Operative Reference Plane (IRP).

The preferred Intra-Operative Reference Plane (IRP) is defined by a line from the anterior superior iliac spine (ASIS) of an operating side to the anterior superior iliac spine (ASIS) of a contralateral side and a line from the acetabular center of the operating side to the anterior superior iliac spine (ASIS) of the operating side.

In a preferred variant of the method, the patient specific morphology information is obtained from two X-ray radiographs, a first of the radiographs being taken substantially from the Anterior-Posterior (AP) direction and a second of the radiographs being taken substantially from the Lateral-Medial (LM) direction.

This allows for an inexpensive and simple acquisition of the required information.

Advantageously, seven anatomical landmarks are defined from the two radiographs, namely e) from the first radiograph the positions of the left and the right teardrops, the position of the anterior superior iliac spine (ASIS) as well as the acetabular center of the operating side of the patient's pelvis;
f) from the second radiograph the position of the anterior superior iliac spine (ASIS), the acetabular center, and the position of the pubic tubercle, all of an operating side of the patient's pelvis.

Alternatively, instead of employing the two, radiographs as described above, the information is obtained by other known techniques such as e. g. CT radiography or MRI, or even a statistical shape model based model instantiation.

For calibrating the alignment of an acetabular component in total hip arthroplasty, the patient specific calibration parameters are obtained as described above. Subsequently, an acetabular component alignment device is independently adjusted depending on the values of the first and the second parameter of the set of calibration parameters.

A preferred inventive method for obtaining patient specific morphology information for alignment of an acetabular component in total hip arthroplasty, comprises the step of acquiring the position of the following anatomical landmarks:

g) the position of the anterior superior iliac spine (ASIS) of an operating side of the patient's pelvis,
h) the geometric centers of both the pubic tubercles
i) the acetabular center of the operating side of the patient's pelvis;

as well as the further step of computing an angle between an Intra-Operative Reference Plane (IRP) and the Anterior Pelvic Plane (APP) of the pelvis as well as an orientation of a vector from the acetabular center to the anterior superior iliac spine (ASIS) of an operating side of the patient's pelvis from the seven positions.

The determined patient-specific morphology can be used not only to compute the calibration parameters for the patient-specific acetabular component alignment device as described above or similar devices but also e. g. in a computer-assisted THA navigation system to eliminate the acquisition of two important landmarks, i. e., the contralateral anterior superior iliac spine and the symphysis, whose acquisition has posted a clinical challenge especially for the so-called image-free THA navigation system. Thus, the invention substantially simplifies a computer-assisted, image-free navigation system for THA.

Preferably, the patient specific morphology information is obtained from two X-ray radiographs, a first of the radiographs being taken substantially from the Anterior-Posterior (AP) direction and a second of the radiographs being taken substantially from the Lateral-Medial (LM) direction, whereas j) the position of the anterior superior iliac spine (ASIS), of the pubic tubercle, and of the acetabular center of the operating side of the patient's pelvis are identified in both radiographs,
k) the positions of both the left and the right teardrops are identified in the second radiograph.

Other advantageous embodiments and combinations of features come out from the detailed description below and the totality of the claims.

BRIEF DESCRIPTION OF THE DRAWINGS

The drawings used to explain the embodiments show.

In the figures, the same components are given the same reference symbols.

PREFERRED EMBODIMENTS

Figure 1:
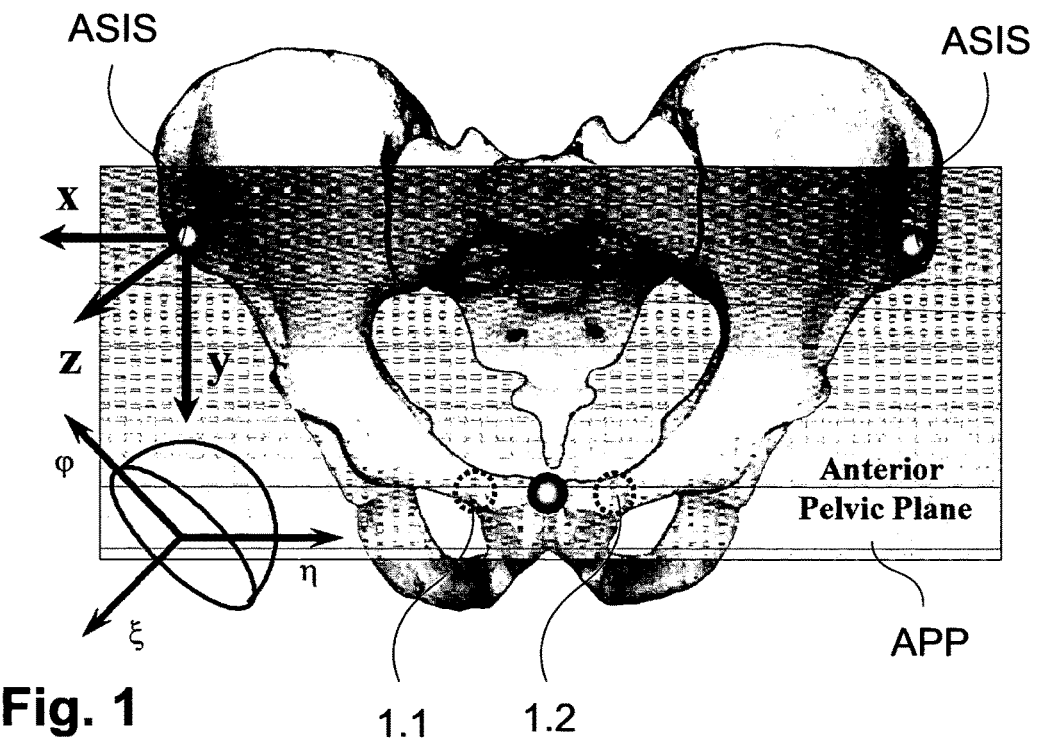
FIG. 1 Definition of the pelvic coordinate system. This is defined by three landmarks: both anterior superior iliac spines and the geometrical center of the two pubicum tuberculae, which span the Anterior Pelvic Plane (APP).

Throughout the text, we always establish a local coordinate system of a rigid body from a local reference plane defined on the rigid body. Thus, without explicitly stating, we always name the local coordinate system after the local reference plane. Furthermore, a vector V that is defined in a local coordinate system X will be noted as $V^X$. But if we would like to know the axis v of a local coordinate system X in another local coordinate system Y, we will note it as $v_X^Y$. A rigid body transformation from a local coordinate system X to another local coordinate system Y will be noted as $T_X^Y$. The inverse of this transformation will be recorded as $T_Y^X$. As in most of the time, we are only interested in knowing the orientation of a vector in a local coordinate system, knowing rotational part $R_X^Y$ of the rigid body transformation $T_X^Y$ is enough for our purpose. For a better explanation, here is a list of the names of the coordinate systems and the vectors:

APP: Anterior Pelvic Plane
IRP: Infra-operative Reference Plane
IDP: Instrument Design Plane
G: A vector indicating the constant direction of the force of gravity
VI: A vector indicating the direction of the virtual instrument axis. The virtual instrument is an imagined instrument that will place a cup in a targeted orientation with respect to one given pelvis. When the cup is placed in the targeted orientation, the direction of the virtual instrument axis is aligned with the normal of the cup opening plane.
CA: A vector indicating the direction from the acetabular center to the ASIS of the operating side of a given pelvis.
IAP: Instrument Alignment Plane
IIAP: Intermediate Instrument Alignment Plane Jamaraz (Jaramaz B, DiGioia A M 3rd, Blackwell M, Nikou C: Computer assisted measurement of cup placement in total hip replacement. Clin Orthop. 354:70, 1998) and Langlotz (Langlotz U, Lawrence J et al: Image guided cup placement. P. 717 In Lemke H, Vannier M, Inamura K, Farmer M (eds): 13$^{th}$ International Congress CARS'99, Elsevier Science B.V., Amsterdam, 1999) introduced the APP concept for measuring anteversion and inclination of the acetabular cup in their computer assisted acetabular cup placement system. The APP is a reference plane of the human pelvis and thus, allows the exact definition of a corresponding three-dimensional (3D) coordinate system. It is based on three landmarks: both anterior superior iliac spines (ASIS) and the geometric center 1.1, 1.2 of two pubic tubercles. The pelvic x-axis points to the patient's right, parallel with the line between the iliac spine points. The y-axis points inferior, perpendicular to the other axes. The angular orientation of the acetabular component can be directly put into relation to the APP (See FIG. 1 for details).

Figure 2:
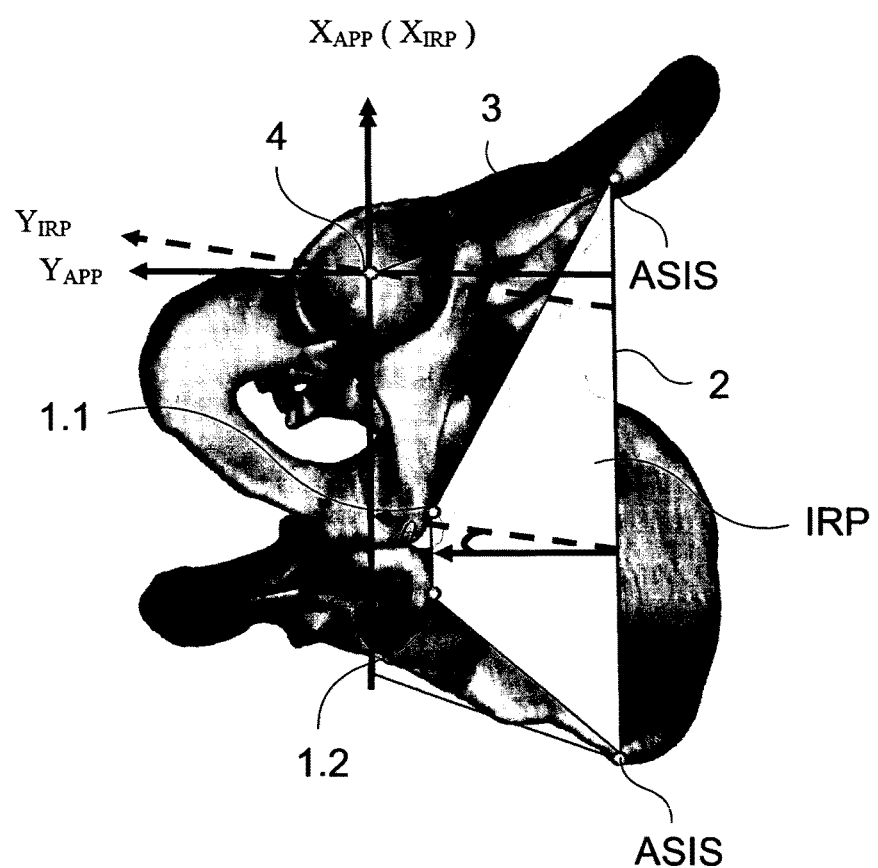
FIG. 2 The relationship between the APP and the IRP. The IRP is defined by two lines: the line from the ASIS of the operating side to the ASIS of the contralateral side and the line from the acetabular center of the operating side to the ASIS of the operating side.

It is difficult, if it is not impossible, to locate the orientation of the APP without using a positional tracking device, largely due to the difficulty in mechanically aligning the geometric center of two pubic tubercles. In this work, we proposed and used a novel reference plane that is called Intra-operative Reference Plane (IRP), which is defined by two lines that can be mechanically aligned with the design of our instrument: the line 2 from the ASIS of the operating side to the ASIS of the contralateral side and the line 3 from the acetabular center 4 of the operating side to the ASIS of the operating side. Similar to how we establish a 3D coordinate system in the APP, we also establish a 3D coordinate system on the IRP, as shown in FIG. 2, where we translate the origins of both coordinate systems to the acetabular center 4 of the operating side. As we are only interested in the orientation of the acetabular component, such a translation does not affect our analysis and computation below. The x-axis of the IRP local coordinate system has the same orientation as the x-axis of the APP local coordinate system, while the y-axis of the IRP local coordinate system is chosen to be a vector that is inside the IRP and perpendicular to the x-axis. The z-axis of the IRP local coordinate system can be computed from the cross product of the x-axis and the y-axis of the IRP local coordinate system.

Figure 3:
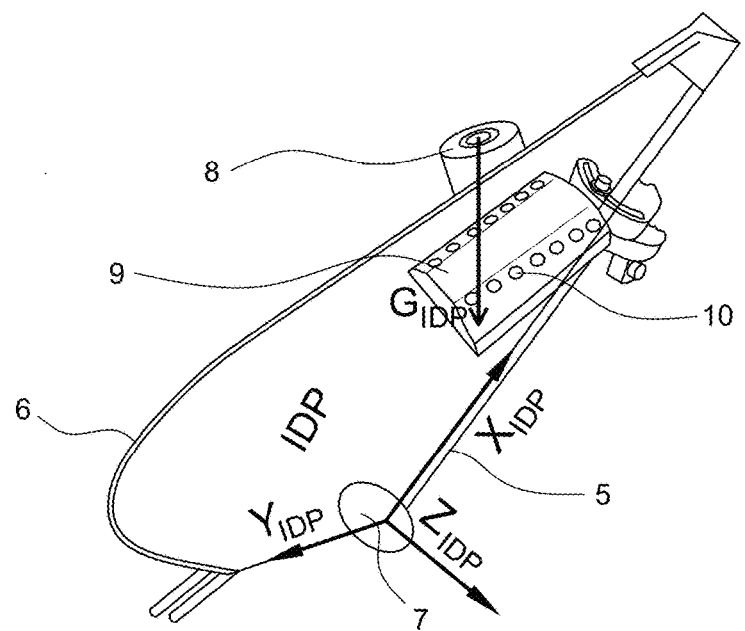
FIG. 3 The definition of the IDP and the alignment device.
Figure 4A:
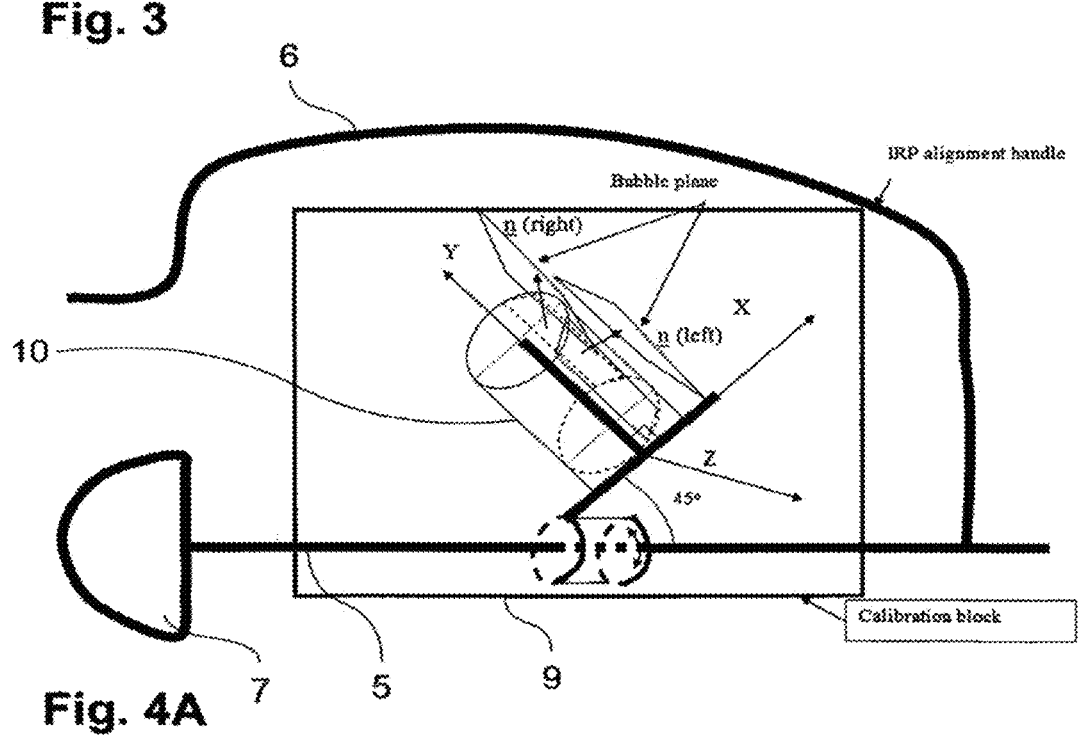
FIG. 4A, B The design and the prototype of an alignment device according to the invention.

The so-called Instrument Design Plane (IDP) is a plane that is defined by the instrument design. Physically, it is defined by the instrument axis 5 and the pitch pointer handle 6, as shown in FIG. 3. As shown in FIG. 4a, the rod along the instrument axis 5 and the alignment component in form of pointer handle 6 meet at a attachment point 13. The pitch pointer handle 6 is designed to be always inside the IDP and to be freely rotated around a fixed axis that is perpendicular to the IDP. Using the IDP, we then establish a local coordinate system as follows. The origin of this local coordinate system is chosen to be the center of the attached cup 7; the x-axis is chosen to be the instrument axis 5 and the y-axis is defined as a vector that is inside the IDP and perpendicular to the x-axis. The z-axis of the IDP local coordinate system can be computed from the cross product of the x-axis and the y-axis of the IDP local coordinate system.

Instrument Calibration for One Given Pelvis

Instrument calibration here means to define the orientation of the bull's-eye bubble level 8 that is attached via pin 11 to the instrument with respect to the local coordinate system of the IDP for a given pelvis, so that when the given pelvis is placed in strict lateral decubitus and when the bubble level is in the center, the instrument axis 5 should be aligned with the targeted orientation of the cup 7. Furthermore, we define the given pelvis as the calibration pelvis and note it as CAL-P.

Without loss of generality, let's assume that the x-axis of the IRP of the given pelvis is (1, 0, 0), the y-axis of the IRP is (0, 1, 0), and the z-axis is (0, 0, 1). We also assume that we know the orientation of the line from the acetabular center to the ASIS of the operating side with respect to the local coordinate system of the IRP, which is defined as $^{CAL\text{-}P}CA^{IRP}$. For a given pelvis, we can measure the angle $^{CAL\text{-}P}\theta$ between the APP and the IRP of the pelvis. Using this angle, we can find the rotation between the local coordinate system of the IRP and the local coordinate system of the APP, $^{CAL\text{-}P}R_{APP}^{IRP}(^{CAL\text{-}P}\theta)$ and the inverse rotation $^{CAL\text{-}P}R_{APP}^{IRP}(^{CAL\text{-}P}\theta)$.

At the same time, given a targeted orientation, we can construct a virtual instrument with respect to the APP of the calibration pelvis using the method introduced by Murray (Murray D W: The definition and measurement of acetabular orientation. J Bone Joint Surg [Br] 75-B: 228-232, 1993) and we call this vector as $^{CAL\text{-}P}VI^{APP}$. This vector can be transformed to the local coordinate system of the IRP using the rotation matrix $^{CAL\text{-}P}R_{APP}^{IRP}(^{CAL\text{-}P}\theta)$.

$$^{CAL\text{-}P}VI^{IRP} = {}^{CAL\text{-}P}R_{APP}^{IRP}(^{CAL\text{-}P}\theta)^{Cal\text{-}P}VI^{APP} \quad (1)$$

When the acetabular cup would be placed in the targeted orientation, the axis of the real instrument should be aligned with $^{CAL\text{-}P}VI^{APP}$, and at the same time, we also require that A) the pelvis should be placed in strict decubitus, which means that the line from the ASIS of the operating side to the ASIS of the contralateral side of the calibration pelvis should be parallel to the constant direction of the force gravity (but with opposite direction); and B) the pitch pointer should be aligned with the ASIS of the operating side of the calibration pelvis. According to the requirement A), the constant direction of the force of gravity in the IRP can be represented as:

$$^{CAL\text{-}P}G^{IRP} = [-1\ 0\ 0] \quad (2)$$

According to the requirement B), we can use the vector $^{CAL\text{-}P}VI^{IRP}$ and the vector $^{CAL\text{-}P}CA^{IRP}$ to construct an instrument alignment plane (IAP), to which the IDP should be aligned in order to place the cup in the targeted orientation. Thus, at this moment, the orientations of the axes of the local coordinate system of the IDP (IAP) with respect to the local coordinate system of the IRP of the calibration pelvis are:

$$\begin{cases} ^{Cal\text{-}P}x_{IDP}^{IRP} = {}^{CAL\text{-}P}VI^{IRP} \\ ^{Cal\text{-}P}z_{IDP}^{IRP} = \dfrac{^{CAL\text{-}P}VI^{IRP} \times {}^{CAL\text{-}P}CA^{IRP}}{|^{CAL\text{-}P}VI^{IRP} \times {}^{CAL\text{-}P}CA^{IRP}|} \\ ^{Cal\text{-}P}y_{IDP}^{IRP} = {}^{Cal\text{-}P}z_{IDP}^{IRP} \times {}^{Cal\text{-}P}x_{IDP}^{IRP} \end{cases} \quad (3)$$

And the rotation from the local coordinate system of the IRP to the local coordinate system of the IDP is:

$$^{CAL\text{-}P}R_{IRP}^{IDP} = [^{Cal\text{-}P}R_{IDP}^{IRP}]^T = [^{Cal\text{-}P}x_{IDP}^{IRP}\ ^{Cal\text{-}P}y_{IDP}^{IRP}\ ^{Cal\text{-}P}z_{IDP}^{IRP}]^T \quad (4)$$

We thus can transform the constant direction of the force of gravity from the local coordinate system of the IRP to the local coordinate system of the IDP:

$$^{CAL\text{-}P}G^{IDP} = {}^{Cal\text{-}P}R_{IRP}^{IDP} \cdot {}^{CAL\text{-}P}G^{IRP} \quad (5)$$

We could then further compute the three angles between $^{CAL\text{-}P}G^{IDP}$ with all three axes of the local coordinate system of the IDP. Given an arbitrary fixation point on the instrument, these three angles will uniquely determine an alignment direction along which the bull's-eye bubble level should be placed so that when the bubble level is in the center, the cup is placed in the targeted orientation.

Compensation for Morphological Differences Between the Calibration Pelvis and the Future Navigation Pelvis As clearly indicated in above calibration procedure, the instrument calibration is a patient-specific task. The exact decomposition of the constant direction of the force of gravity with respect to the three axes of the local coordinate system of the IDP depends on two patient-specific morphological information: A) the angle θ between the APP and the IRP of the pelvis; and B) the orientation of the vector from the acetabular center to the ASIS of the operating side of the pelvis in the local coordinate system of the IRP of the navigation pelvis. For a future navigation pelvis, i. e. for the pelvis of the patient to be operated, it may have different morphological information from the calibration pelvis.

Without compensation for such differences, the calibrated instrument may not place the cup in the targeted position when the attached bull's-eye bubble level is in the center and all other requirements as described above are satisfied. Bull's-eye bubble levels are commercially available. They are indicators for an inclination against a horizontal plane, i. e. in 2 dimensions. Usual bull's-eye bubble levels are provided with an attachment pin being perpendicular to the reference plane, i. e. if the bubble level is in its central position, the pin points downwards in the direction of the force of gravity. The indication range of usual bull's eye bubble levels is about 5°.

Due to the fact that we require that the future navigation pelvis should be placed in strict lateral decubitus, we can assume that the IRP of the future navigation pelvis is aligned with the IRP of the calibration pelvis. The requirement of the navigation pelvis being in strict lateral decubitus may be checked by means that are known as such, e. g. by a further bull's-eye bubble level directly affixed to the navigation pelvis.

Thus, similar to what we have done for the calibration pelvis, we can also establish an exactly same local coordinate system of the IRP of the future navigation pelvis as follows. We regard this coordinate system as a global coordinate system for both the calibration and the navigation. In this global coordinate system, the x-axis is defined as (1, 0, 0), which is parallel to the gravity direction but with opposite direction; the y-axis is defined as (0, 1, 0), which is a vector inside the IRP and perpendicular to the x-axis.

In this section, we also assume that we know the patient-specific morphological information for the future navigation pelvis, i. e., we know the angle between the IRP and the APP of the navigation pelvis, which we called it $^{NAV\text{-}P}\theta$, and we know the orientation of the vector from the acetabular center to the ASIS of the operating side of the navigation pelvis, which we note it as $^{NAV\text{-}P}CA^{IRP}$. Such patient-specific morphological information can be derived from measurements such as a pre-operative CT or MRI scan, or even a statistical shape model based model instantiation. In this invention, we also present a method to extract the patient-specific morphological information from two conventional X-ray radiographs as described below.

Given the angle $^{NAV\text{-}P}\theta$ between the IRP and the APP of the navigation pelvis, we can compute a rotation between the local coordinate system of the IRP and the local coordinate system of the APP of the navigation pelvis, $^{NAV\text{-}P}R_{APP}^{IRP}(^{NAV\text{-}P}\theta)$ and the inverse rotation $^{NAV\text{-}P}R_{APP}^{IRP}(^{NAV\text{-}P}\theta)$.

Similar to what we have done for the calibration pelvis, we can also construct a virtual instrument for the navigation pelvis according to a given targeted cup orientation. As the orientation of this virtual instrument is measured with respect to the APP of the navigation pelvis, we need to transform it from this local coordinate to the global coordinate system using the rotation matrix $^{NAV\text{-}P}R_{APP}^{IRP}(^{NAV\text{-}P}\theta)$.

$$^{NAV\text{-}P}VI^{IRP} = {^{NAV\text{-}P}R_{APP}^{IRP}}(^{NAV\text{-}P}\theta) \cdot {^{NAV\text{-}P}VI^{APP}} \quad (6)$$

Figure 4B:
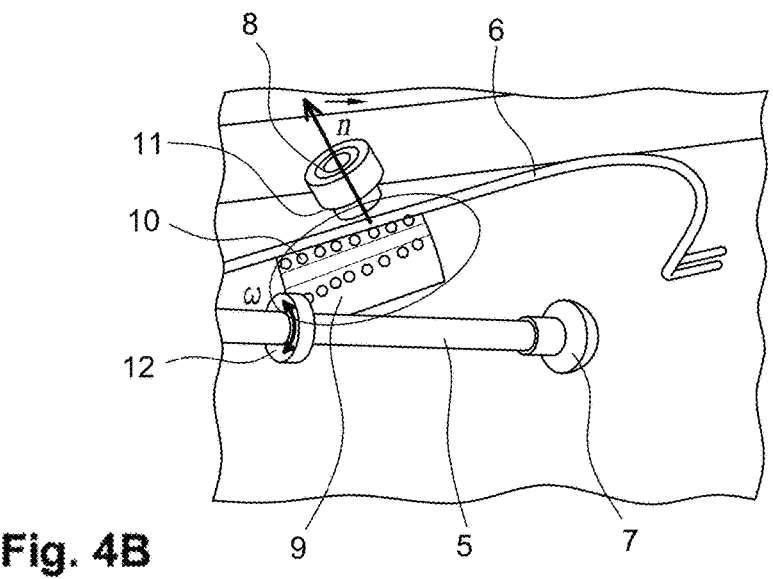

As both $^{CAL\text{-}P}CA^{IRP}$ of the calibration pelvis and $^{NAV\text{-}P}CA^{IRP}$ of the navigation pelvis are measured with respect to the global coordinate system defined on the aligned IRPs of two pelvises, we can first construct an Intermediate Instrument Alignment Plane (IIAP) using $^{NAV\text{-}P}VI^{IRP}$ and $^{CAL\text{-}P}CA^{IRP}$, and establish a local coordinate system on it as follows. The x-axis of the IIAP is defined as the vector $^{NAV\text{-}P}VI^{IRP}$; the y-axis is a vector inside the IIAP and perpendicular to the x-axis. When the IIAP is compared to the IAP of the calibration pelvis, which is constructed through the vector $^{CAL\text{-}P}VI^{IRP}$ and the vector $^{CAL\text{-}P}CA^{IRP}$, the two planes have different orientations due to the difference on the orientations of the vector $^{NAV\text{-}P}VI^{IRP}$ and the vector $^{CAL\text{-}P}VI^{IRP}$. Similar to what we have done for calibration pelvis, we can first rotate the constant direction of the force of gravity, which always points to the negative x-direction of the global reference coordinate system, from the global reference coordinate system to the local coordinate system established on the IIAP of the navigation pelvis. Thus, the transformed orientation of the constant direction of the force of gravity in the local coordinate system of the alignment plane in this case will be different from the case when it is transformed to the alignment plane of the calibration pelvis. One important observation about such a difference is that it only depends on the difference between the angle $^{NAV\text{-}P}\theta$ and the angle $^{CAL\text{-}P}\theta$. When the calibration pelvis is selected, such a difference will be a function continuously depending on the angle $^{NAV\text{-}P}\theta$ of the future navigation pelvis. Furthermore, depending on the accuracy requirement, we even can discretize this continuous function so that we only need to compute the transformed orientations of the constant direction of the force of gravity in a limited number of control angles $\{^{NAV\text{-}P}\theta_i\}$ and call these angles the calibration angles. The transformed gravity direction for any given angle can be obtained approximately by taking the transformed gravity direction of a calibration angle which is closest to the given angle. A hardware design implementing this idea has been done and is shown in FIGS. 3 and 4, where the holes 10 on the calibration block 9 show the alignment directions for placing the bubble gauge 8 for a limited number of calibration angles $\{^{NAV\text{-}P}\theta_i\}$ arranged with an interval of 5° in the range between 20° and 50°.

However, until now, we still have not completely solved the morphological difference compensation problem due to the use of the vector $^{CAL\text{-}P}CA^{IRP}$ to construct the IIAP. Observing that the true instrument alignment plane for the navigation pelvis, which is constructed by the vector $^{NAV\text{-}P}VI^{IRP}$ and the vector $^{NAV\text{-}P}CA^{IRP}$, is different from the IIAP by only a rotation around the vector $^{NAV\text{-}P}VI^{IRP}$. We can compensate such a difference by applying a rotation around the vector $^{NAV\text{-}P}VI^{IRP}$ to the IIAP so that it will finally be aligned with the IDP of the navigation pelvis. The exact amount of the rotation around the vector $^{NAV\text{-}P}VI^{IRP}$ to be applied can be estimated from the given morphological information of the future navigation pelvis and that of the calibration pelvis. From an instrument design point of view, such a rotation is equivalent to rotate the instrument alignment plane around the instrument axis. In the context of the embodiment shown in FIGS. 3 and 4 the calibration block 9 can be rotated around the instrument axis 5 for a compensation of the difference between the vector $^{NAV\text{-}P}CA^{IRP}$ of the navigation pelvis and the vector $^{CAL\text{-}P}CA^{IRP}$ of the calibration pelvis.

As mentioned, the calibration block 9 with a set of discrete calibration holes 10 can be rotated around the instrument axis 5. The orientation of each calibration hole 10 is computed according to the associated calibration angle $^{NAV\text{-}P}\theta_i$ so that when the bubble level is placed inside the associated hole and when all other requirements are satisfied, the cup should be place in a targeted orientation with respect to the patient's APP. The rotation of this calibration block 9 around the instrument axis 5 is used to further compensate the morphological difference between the vector $^{NAV\text{-}P}CA^{IRP}$ of the navigation pelvis and the vector $^{CAL\text{-}P}CA^{IRP}$ of the calibration pelvis.

Figure 5A:
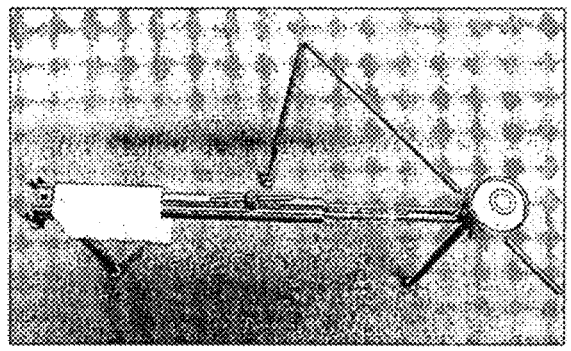
FIG. 5 The alignment device for image acquisition and a schematic drawing how it works.
Figure 5B:
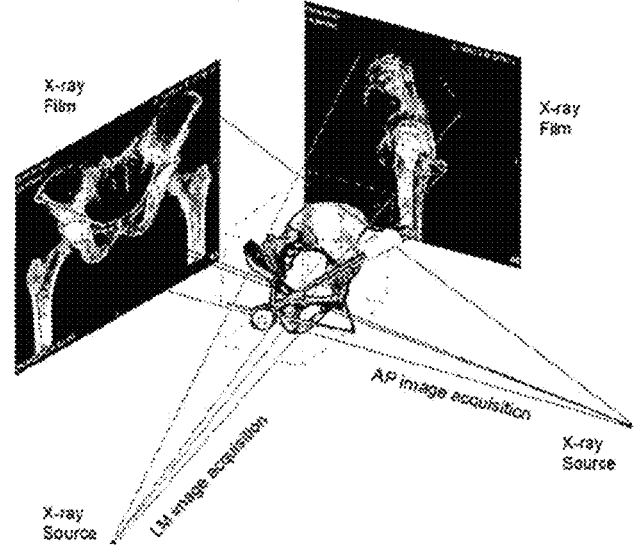
Figure 6:
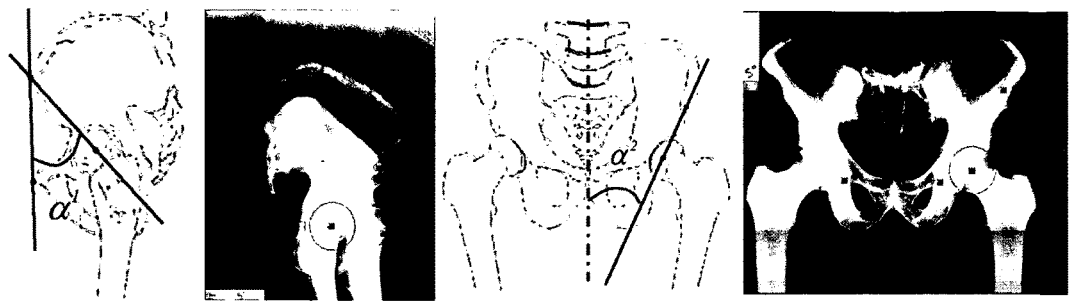
FIG. 6 User interface and landmarks used for computing the patient-specific morphology information.
Figure 7A:
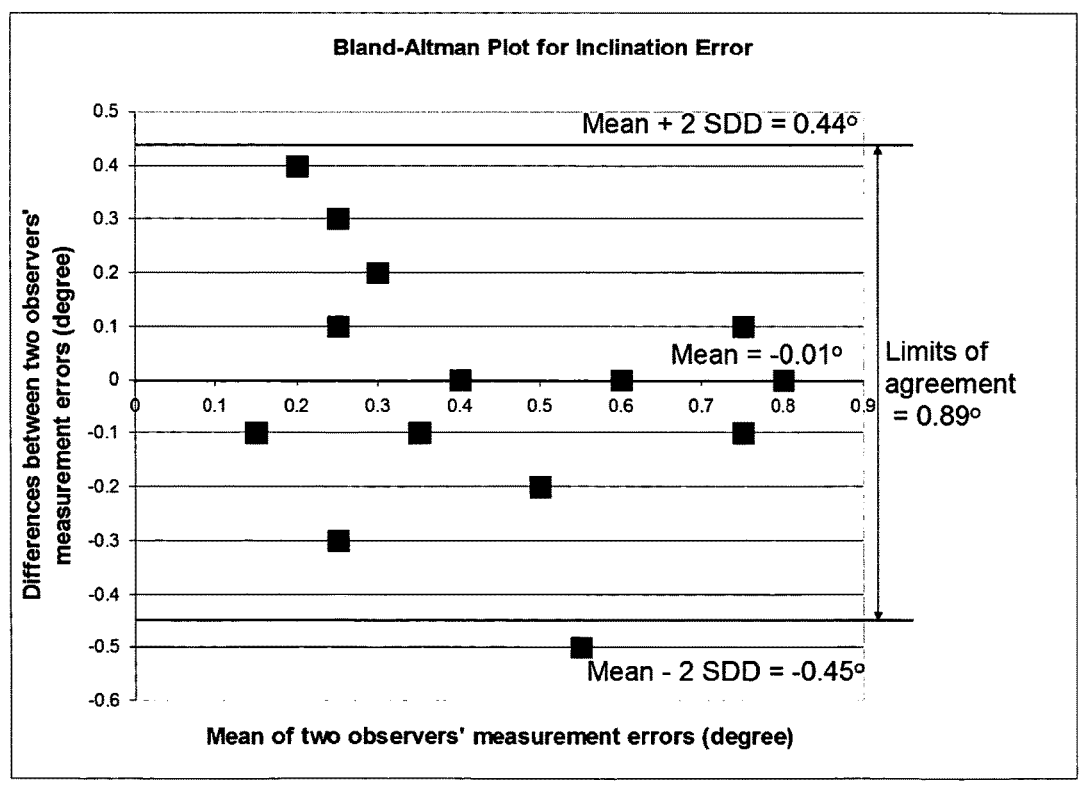
FIG. 7A, B Bland-Altman plot for inclination (a) and anteversion (b) errors of two observers.
Figure 7B:
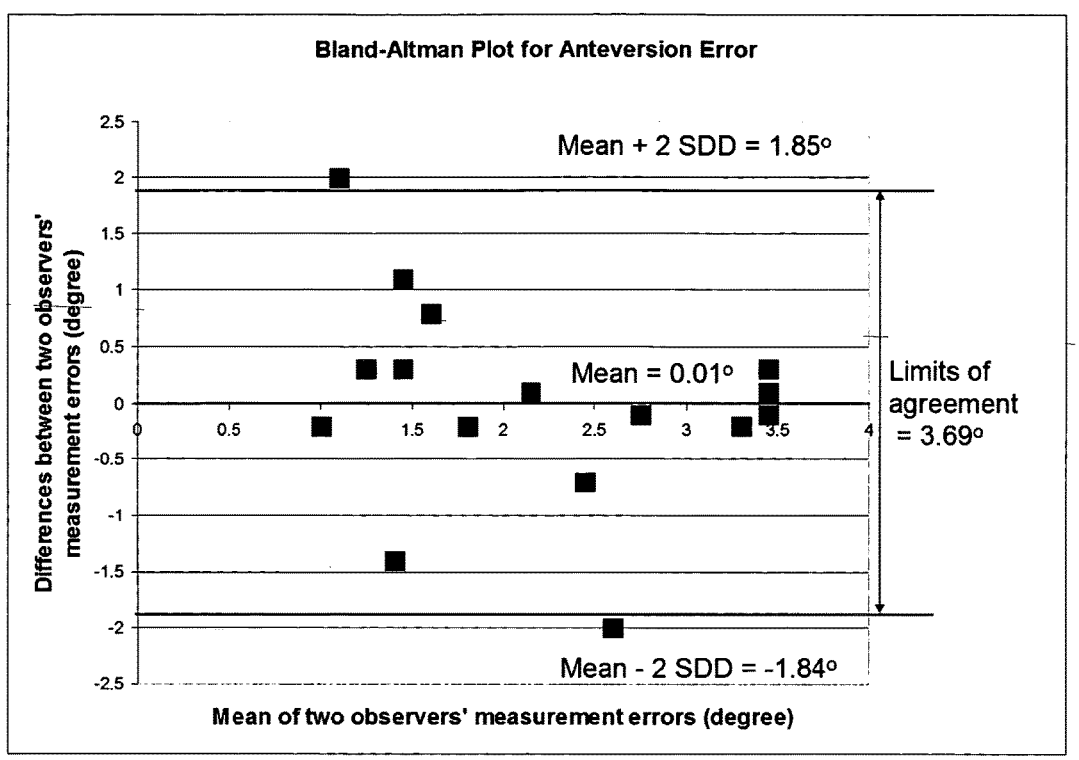

Method and Device for Determining Patient-Specific Morphology Information from Two X-Ray Radiographs Knowing the patient-specific morphology information of the future navigation pelvis is important for the calibration of the alignment device. Such information can be easily obtained from a CT or a MRI scan, or even from a statistical shape model based model instantiation. Here we present a method and a device for determining the patient-specific morphology information from two X-ray radiographs comprising steps:

a) Acquiring two conventional X-ray radiographs using an alignment device shown in FIG. 5, with one image acquired from the Anterior-Posterior (AP) direction and the other acquired from the Lateral-Medial (LM) direction. The alignment device is used to control the positioning of the patient so that (1) when the AP radiograph is acquired, the APP of the patient will be roughly parallel to the imaging plane of the X-ray machine; and (2) when the LM radiograph is acquired, the APP should be aligned with the X-ray projection beam.

b) Interactively defining seven anatomical landmarks from the acquired images. FIG. 6 shows the landmarks (green spheres) and the interface for a cadaver pelvis. The landmarks defined from the LM radiograph (FIG. 6, left) are the position of the anterior superior iliac spine (ASIS), the acetabular center, and the position of the pubic tubercle, all of the operating side of the patient's pelvis. The landmarks from the AP radiograph (FIG. 6, right) are the positions of the left and right teardrops, and the position of the anterior superior iliac spine (ASIS) as well as the acetabular center of the operating side of the patient's pelvis.

c) Computing a patient-specific morphology based on the defined landmarks. Using those seven landmarks that are separately digitized from the two X-ray radiographs (3 landmarks from the LM image and 4 landmarks from the AP image), we can first compute two separate angles as shown in FIG. 6: $\alpha^1$ from the LM image and $\alpha^2$ from the AP image. The angle between the IRP and the APP of the navigation pelvis is the angle $\alpha^1$, i.e., $^{NAV-P}\theta = \alpha^1$. The orientation of the vector from the acetabular center to the ASIS of the operating side of the future navigation pelvis with respect to the local coordinate system of the APP is computed according to following equation:

$$^{NAV-P}CA^{APP} = [\pm\tan(\alpha^2) 1.0 \pm \tan(\alpha^1)] \quad (7)$$

where the signs in the equation depend on the operating sides (left or right).

Experiments

We have conducted following experiments to validate the methods and devices proposed in this invention:

(1) A cadaver pelvis experiment to evaluate the accuracy and the sensitivity of our invention to the orientation of the pelvis with respect to the X-ray table during image acquisition. In this experiment, using the image acquisition alignment device, we acquired four AP images when the pelvic APP was positioned in 0, 5, 10, and 15 degree with respect to the X-ray table, and another four LM images when the normal of the pelvic APP was positioned in 0, 5, 10, and 15 degree with respect to the X-ray table. Combining the four AP images with the four LM images, we totally obtained 16 pairs of images as the input to our calibration program. Two observers (one senior surgeon and one engineer) participated in the validation experiment. The computed alignment angles (anteversion and inclination) were then compared to the associated ground truths, which were obtained with a CT-based method.

(2) A plastic pelvis experiment to evaluate the accuracy and reproducibility of our invention, taking the measurement from a hybrid navigation system combining percutaneous pointer-based digitization and fluoroscopy-based landmark reconstruction as the reference. Two observers (one senior surgeon and one engineer) participated in the validation experiment. Each observer performed 10 times cup placements using the methods and devices proposed in this invention. Each time, when the bubble level is placed in the center, the measurement from the navigation system was recorded.

(3) A preliminary clinical trail to evaluate the accuracy and the usability of our invention, taking the measurement from an image-free navigation system as the reference.

Please keep it in mind that the morphology information of the pelvis that we used for the calibration as described in Section 2.2.2 is obtained from an average model computed from 48 pelvis models.

Results

Results for the First Experiment

Table 1 and 2 shows the inclination error and the anteversion error for the first observer when our system was evaluated on the cadaver data. A mean inclination error of 0.4+/−0.2 degree and a mean anteversion error of 2.2+/−0.9 degree were observed. The inclination error and the anteversion error for the second observer are shown in Table 3 and 4, respectively. A mean inclination error of 0.5+/−0.3 degree and a mean anteversion error of 2.2+/−1.1 degree were observed. To assess the inter-observer variability, the difference between the measurement errors of both observes was calculated. Bland-Altman calculations were performed using Microsoft Office Excel 2003. The mean difference and the standard deviation of the difference (SDD) were calculated. Results were plotted in FIGS. 8(a) and (b) for inclination and anteversion errors, respectively, showing the 95% limits of agreement (mean difference+/−2 SDDs). The mean difference for the inclination error is −0.01 degree with the 95% limits of agreement of 0.89 degree, while the mean difference for the anteversion error is 0.01 degree with the 95% limits of agreement of 3.69 degree.

TABLE 1

Inclination error for observer #1

| AP Images | LM Images | | | | |
|---|---|---|---|---|---|
| | LM_0 | LM_5 | LM_10 | LM_15 | Mean ± SD |
| AP_0 | 0.4 | 0.4 | 0.3 | 0.4 | 0.4 ± 0.1 |
| AP_5 | 0.1 | 0.8 | 0.4 | 0.3 | 0.4 ± 0.3 |
| AP_10 | 0.1 | 0.4 | 0.3 | 0.3 | 0.3 ± 0.1 |
| AP_15 | 0.8 | 0.6 | 0.7 | 0.8 | 0.7 ± 0.1 |
| Mean ± SD | 0.4 ± 0.3 | 0.6 ± 0.2 | 0.4 ± 0.2 | 0.5 ± 0.2 | 0.4 ± 0.2 |

TABLE 2

| AP Images | LM Images | | | | |
|---|---|---|---|---|---|
| | LM_0 | LM_5 | LM_10 | LM_15 | Mean ± SD |
| AP_0 | 2.1 | 2.0 | 1.6 | 2.0 | 1.9 ± 0.2 |
| AP_5 | 0.7 | 3.4 | 2.1 | 1.6 | 2.0 ± 1.1 |
| AP_10 | 0.9 | 2.2 | 1.4 | 1.7 | 1.6 ± 0.5 |
| AP_15 | 3.5 | 2.7 | 3.2 | 3.6 | 3.3 ± 0.4 |
| Mean ± SD | 1.8 ± 1.3 | 2.6 ± 0.6 | 2.1 ± 0.8 | 2.2 ± 0.9 | 2.2 ± 0.9 |

TABLE 3

Inclination error for observer #2

| AP Images | LM Images | | | | |
|---|---|---|---|---|---|
| | LM_0 | LM_5 | LM_10 | LM_15 | Mean ± SD |
| AP_0 | 0.0 | 0.2 | 0.2 | 0.1 | 0.1 ± 0.1 |
| AP_5 | 0.4 | 0.8 | 0.6 | 0.8 | 0.7 ± 0.2 |

TABLE 3-continued

Inclination error for observer #2

| | LM Images | | | | |
|---|---|---|---|---|---|
| AP Images | LM_0 | LM_5 | LM_10 | LM_15 | Mean ± SD |
| AP_10 | 0.2 | 0.4 | 0.2 | 0.4 | 0.3 ± 0.1 |
| AP_15 | 0.8 | 0.6 | 0.8 | 0.7 | 0.7 ± 0.1 |
| Mean ± SD | 0.4 ± 0.3 | 0.5 ± 0.3 | 0.5 ± 0.3 | 0.5 ± 0.3 | 0.5 ± 0.3 |

TABLE 4

Anteversion error for observer #2

| | LM Images | | | | |
|---|---|---|---|---|---|
| AP Images | LM_0 | LM_5 | LM_10 | LM_15 | Mean ± SD |
| AP_0 | 0.1 | 1.2 | 1.3 | 0.9 | 0.9 ± 0.5 |
| AP_5 | 2.1 | 3.5 | 2.8 | 3.6 | 3.0 ± 0.7 |
| AP_10 | 1.1 | 2.1 | 1.1 | 1.9 | 1.6 ± 0.5 |
| AP_15 | 3.4 | 2.8 | 3.4 | 3.3 | 3.2 ± 0.3 |
| Mean ± SD | 1.7 ± 1.4 | 2.4 ± 1.0 | 2.2 ± 1.2 | 2.4 ± 1.3 | 2.2 ± 1.1 |

Results for the Second Experiment

The following table shows the difference between the target cup orientation when the bubble level is in the center and the measurements recorded from the navigation system:

| | Errors | |
|---|---|---|
| Observers | Anteversion (°) | Inclination (°) |
| Observer #1 | 0.5 ± 1.1 | 0.4 ± 0.7 |
| Observer #2 | 0.4 ± 1.0 | 0.4 ± 0.5 |

Results for the Third Experiment

We have evaluated the proposed method and device on three clinical cases. Each time, when the bubble level is placed in the center, the measurement from the navigation system was recorded. The following table shows the differences between the target cup orientation the measurements recorded from the navigation system for all three cases:

| | Errors | |
|---|---|---|
| Case | Anteversion (°) | Inclination (°) |
| Case #1 | 0.7 | 0.9 |
| Case #2 | 6.5 | 0.3 |
| Case #3 | 1.5 | 3.5 |
| Average | 2.9 | 1.5 |

The invention claimed is:

1. An acetabular component alignment device for aligning an acetabular component in total hip arthroplasty (THA) comprising
    (i) a rod extending along a main instrument axis having a first and a second end, wherein said second end comprises an acetabular cup,
    (ii) an alignment component being a curved rod, wherein an inner curvature of the curved rod and the main instrument axis define an instrument design plane (IDP), configured to be able to point to a position of an anterior superior iliac spine (ASIS) of an operating side of a pelvis of a patient, wherein said alignment component is rotably coupled to said rod at an attachment point at said first end of the rod in such a way to allow at least one degree of freedom between said curved rod and said rod,
    (iii) a calibration component that is, separately from the alignment component, attached to said rod between said attachment point and said second end, wherein the rod and the alignment component define the instrument design plane (IDP), wherein the calibration component is rotably and lockably coupled to the rod and rotatable around a fixed axis that is perpendicular to the IDP in such a way to allow at least one degree of freedom between said calibration component and said rod, and wherein the calibration component comprises a calibration block having a cylindrical body that is rotatable around the rod, and including a plurality of differently oriented receptable holes along a longitudinal axis of said body and extending therein in a traversing direction to said longitudinal axis, wherein the receptable holes are spaced longitudinally from each other and radially offset from each other, and
    (iv) a two-dimensional inclination indicator coupled to the calibration block, said two-dimensional inclination indicator comprises at least one of a bull's eye bubble level indicator having an attachment pin, a digital compass and an accelerometer, and wherein the calibration block having the cylindrical body has a plurality of attachment sites defined by the differently oriented receptacle holes comprising at least a first and a second receptacle hole, each configured for coupling to said inclination indicator, wherein the first receptable hole corresponds to a first inclination relative to the rod extending along the instrument main axis and the second receptacle hole corresponds to a second inclination relative to the rod, wherein the first inclination is different from the second inclination, wherein the differently oriented receptacle holes are configured to accommodate the pin of the bubble level indicator.

2. The alignment device as recited in claim 1, comprising a scale configured to relate a rotational position of the calibration block about the instrument main axis to a value of one patient specific calibration parameter, wherein said scale attaches the calibration block to the rod.

3. The alignment device as recited in claim 1, wherein the two-dimensional inclination indicator is configured to indicate an inclination against a horizontal plane.

4. An acetabular component alignment device for aligning an acetabular component in total hip arthroplasty (THA) comprising
    (i) a rod extending along a main instrument axis having a first and a second end, wherein said second end comprises an acetabular cup,
    (ii) an alignment component being a curved rod, wherein an inner curvature of the curved rod and the main instrument axis define an instrument design plane IDP, configured to point to a position of an anterior superior iliac spine (ASIS) of an operating side of the pelvis of the patient, wherein said alignment component is rotably coupled to said rod at an attachment point at said first end of the rod in such a way to allow at least one degree of freedom between said curved rod and said rod,
    (iii) a calibration component that is, separately from the alignment component, coupled to said rod between said attachment point and said second end, wherein the rod and the alignment component define an instrument design plane (IDP), wherein the alignment component is rotably and lockably coupled to said rod about a fixed axis that is perpendicular to the IDP to allow at least one degree of freedom between said calibration component and said rod and wherein the calibration component comprises a calibration block having a cylindrical body including a plurality of differently oriented receptable holes along a longitudinal axis of the body and extending therein in a traversing direction to said longitudinal axis, wherein the receptable holes are spaced longitudinally from each other and radially offset from each other, and (iv) a two-dimensional inclination indicator coupled to the calibration block, said two-dimensional inclination indicator comprises at least one of a bull's eye bubble level indicator having an attachment pin, a digital compass and an accelerometer, and wherein the calibration block having the cylindrical body has a plurality of attachment sites defined by the differently oriented receptacle holes comprising at least a first and a second receptacle hole, each configured for coupling to said inclination indicator, wherein the first receptacle hole corresponds to a first inclination relative to the rod extending along the instrument main axis and the second receptacle hole corresponds to a second inclination relative to the rod, wherein the first inclination is different from the second inclination, wherein the differently oriented receptacle holes are configured to accommodate the pin of the bubble level indicator.

5. The acetabular component alignment device according to claim 1, wherein the alignment component is configured to be independently adjustable depending on values of a first and second patient-specific calibration parameter relating to rotational offsets of the acetabular component during rotation around the main instrument axis.

6. The acetabular component alignment device as recited in claim 1, further comprising a scale fastened to the calibration block and attached to the rod, wherein the scale couples the calibration block to the rod.

7. The acetabular component alignment device as recited in claim 1, further comprising a coupler coupling the alignment component to the rod and configured to allow for the alignment component to be freely rotable around the rod.

* * * * *